United States Patent
Jäntti et al.

(10) Patent No.: US 11,684,279 B2
(45) Date of Patent: Jun. 27, 2023

(54) SYSTEM AND METHOD FOR DETERMINING A PROBABILITY FOR A PERSON TO HAVE ARRHYTHMIA

(71) Applicant: Heart2Save OY, Kuopio (FI)

(72) Inventors: Helena Jäntti, Kuopio (FI); Mika Tarvainen, Kuopio (FI); Jukka Lipponen, Kuopio (FI)

(73) Assignee: Heart2Save Oy, Kuopio (FI)

( * ) Notice: Subject to any disclaimer, the term of this patent is extended or adjusted under 35 U.S.C. 154(b) by 93 days.

(21) Appl. No.: 16/348,008

(22) PCT Filed: Nov. 1, 2017

(86) PCT No.: PCT/FI2017/050753
§ 371 (c)(1),
(2) Date: May 7, 2019

(87) PCT Pub. No.: WO2018/087423
PCT Pub. Date: May 17, 2018

(65) Prior Publication Data
US 2020/0113459 A1    Apr. 16, 2020

(30) Foreign Application Priority Data
Nov. 8, 2016    (EP) ..................................... 16197823

(51) Int. Cl.
*A61B 5/024*    (2006.01)
*G16H 50/30*    (2018.01)
(Continued)

(52) U.S. Cl.
CPC .......... *A61B 5/02438* (2013.01); *A61B 5/366* (2021.01); *A61B 5/681* (2013.01);
(Continued)

(58) Field of Classification Search
CPC ... A61B 5/0472; A61B 5/746; A61B 5/02438; A61B 5/02416; A61B 5/1102;
(Continued)

(56) References Cited

U.S. PATENT DOCUMENTS

2012/0296225 A1    11/2012    Zhang
2015/0065891 A1*   3/2015    Wiesel .................. A61B 5/352
                                                          600/479
(Continued)

FOREIGN PATENT DOCUMENTS

CN    204813838 U    12/2015
CN    204813865 U    12/2015
(Continued)

OTHER PUBLICATIONS

Tuomo, Reiniaho, "International Search Report," prepared for PCT/FI2017/050753, dated Feb. 5, 2018, seven pages.
(Continued)

*Primary Examiner* — Carl H Layno
*Assistant Examiner* — Aya Ziad Bakkar
(74) *Attorney, Agent, or Firm* — Smith, Gambrell & Russell LLP

(57) ABSTRACT

Disclosed are a system and a method for determining a probability for a person to have arrhythmia. The system comprises means for measuring heartbeat interval of the person for a period of time; an accelerometer; means for measuring an electrocardiogram of the person; a user interface for providing information and alerts, and a processor. The processor is configured to detect a period of rest of the person, based on measurement data from the accelerometer; analyze the measured heartbeat interval to determine a probability of having arrhythmia for the person; generate an alert to the user interface, if the probability exceeds a predetermined threshold value, to alert the person to mea-
(Continued)

sure the electrocardiogram with the means for measuring an electrocardiogram; analyze the measured electrocardiogram to determine if the probable arrhythmia is confirmed; and indicate the confirmed arrhythmia to the person via the user interface.

10 Claims, 4 Drawing Sheets

(51) Int. Cl.
  *G16H 50/20*  (2018.01)
  *A61B 5/00*  (2006.01)
  *A61B 5/11*  (2006.01)
  *G16H 40/67*  (2018.01)
  *G16H 40/63*  (2018.01)
  *A61B 5/366*  (2021.01)

(52) U.S. Cl.
  CPC ............ *A61B 5/746* (2013.01); *G16H 40/63* (2018.01); *G16H 40/67* (2018.01); *G16H 50/20* (2018.01); *G16H 50/30* (2018.01); *A61B 5/02416* (2013.01); *A61B 5/1102* (2013.01); *A61B 5/6831* (2013.01)

(58) Field of Classification Search
  CPC ............ A61B 2562/0219; A61B 5/681; G16H 50/30; G16H 50/20; G16H 40/67
  See application file for complete search history.

(56) References Cited

U.S. PATENT DOCUMENTS

| | | | |
|---|---|---|---|
| 2015/0164349 A1* | 6/2015 | Gopalakrishnan ... | A61B 5/0022 600/508 |
| 2015/0374310 A1* | 12/2015 | Lee ...................... | A61B 5/1118 600/483 |

FOREIGN PATENT DOCUMENTS

| | | |
|---|---|---|
| CN | 204813868 U | 12/2015 |
| EP | 0841034 A1 | 5/1998 |
| WO | WO-2015107521 A1 | 7/2015 |
| WO | WO-2015126459 A1 | 8/2015 |
| WO | WO-2016161152 A1 | 10/2016 |

OTHER PUBLICATIONS

Hu, Sheng, et al., "A Real-Time Cardiac Arrhythmia Classification System With Wearable Electrocardiogram," 2011 International Conference on Body Sensor Networks, IEEE Conference, 2011, pp. 119-124.

Nguyen, Thanh-Binh, et al., "Individualized Arrhythmia Detection with ECG Signals From Wearable Devices," Centre for Pattern Recognition and Data Analytics, Deakin University, 2014, seven pages.

* cited by examiner

SYSTEM AND METHOD FOR DETERMINING A PROBABILITY FOR A PERSON TO HAVE ARRHYTHMIA

TECHNICAL FIELD

The present disclosure relates generally to determination of a medical condition; and more specifically, to a system and a method for determining probability of arrhythmia for a person.

BACKGROUND

Conventionally, issues such as hypertension, diabetes, obesity, poor diet, excessive alcohol intake and so forth are known to cause health conditions in people. Such health conditions may include narrowing, deformation and clotting of blood vessels, further leading to diseases such as cardiovascular and cerebrovascular diseases. A cerebrovascular disease is a disease that affects the blood vessels that supply blood to the brain. Such diseases may include a cerebrovascular accident (CVA or stroke), which is one of the leading causes of fatality and disability in people around the world. Stroke generally occurs due to insufficient blood supply to the brain, causing a supply of oxygen and nutrients to the brain to be limited or stopped, which may lead to death of brain cells.

Strokes may include ischemic strokes that are caused by a blood clot blocking blood supply to the brain and hemorrhagic strokes that are caused by a blood vessel supplying blood to the brain to be ruptured, preventing blood flow to the brain. Further, causes of ischemic strokes include blockage of blood supply by debris originating elsewhere in the body, usually in the heart (an embolic stroke), blockage of blood supply to the brain due to a blood clot forming in the brain vessels (thrombotic stroke), decrease in blood supply to all parts of the brain (cerebral hypoperfusion) and so forth. Generally about 30% of strokes are embolic strokes (from cardiac origin) and 70% of strokes are ischemic (narrowing of cerebral vessels).

Around every third stroke is caused by conditions such as cardiac arrhythmia (or cardiac dysrhythmia). Cardiac arrhythmia relates to a condition of heart rhythm unrelated to or uncontrolled by current hemodynamic state. Arrhythmias include, tachycardia or fast heart rate (over 100 beats per minute in adults), bradycardia or slow heart rate (below 40-60 beats per minute in adults depending on individual factors) and irregular heart rate, most usually atrial fibrillation. Very fast or very slow heart rhythm can lead to cerebral hypoperfusion and atrial fibrillation can cause blood clot formation in the heart leading to embolic stroke. Often cardiac arrhythmias do not make any noticeable symptoms, and thus detection of such condition is challenging. Further, the symptoms may appear irregularly, for example, once a week for a few minutes or hours. Noticing such irregular symptoms may be challenging, which predisposes the affected person to a possible stroke. Traditionally cardiac arrhythmia is detected using electrocardiography (ECG), i.e. the process of recording electrical activity of the heart over a period of time using electrodes placed on limbs and chest of a person. However, a person may undergo the ECG procedure only in presence of noticeable symptoms, such as palpitations, chest pains, shortness of breath, fluttering in chest, sweating, fainting and so forth. Additionally, conducting regular ECG procedure for monitoring cardiac arrhythmia may not be feasible.

Document CN 204813865 U discloses a system comprising means for measuring heartbeat interval, means for measuring an electrocardiogram, a user interface and a processor analyzing the measurement results. The document does however neither disclose using threshold values for predicting a probability of having arrhythmia, nor the use of an accelerometer in order to determine an optimal time for measurement of the heartbeat interval. Document CN 204813868 U relates to a cardiovascular health checkout gear comprising a control circuit, an inflating pulse pressurized bandage, a pump a pair of electrodes. The aim is to control blood pressure. Document WO 2016/161152 discloses a wearable device for monitoring and diagnosing cardiovascular conditions of a wearer, such as heart rate, motion or blood oxygenation.

Therefore, in light of the foregoing discussion, there exists a need for a better method to monitor and detect cardiac arrhythmias.

SUMMARY

The present disclosure seeks to provide a system for determining a probability of arrhythmia for a person. The present disclosure also seeks to provide a method for determining a probability of arrhythmia for a person. The present disclosure seeks to provide a solution to the existing problems of inconvenient and inefficient determination of arrhythmia. An aim of the present disclosure is to provide a solution that overcomes at least partially the problems encountered in prior art, and enables efficient determination of probable arrhythmia conditions.

In one aspect, an embodiment of the present disclosure provides a system for determining a probability of arrhythmia for a person, comprising
  a wearable device comprising
    means for measuring heartbeat interval of the person for a period of time;
    an accelerometer;
  means for measuring an electrocardiogram of the person;
  a user interface for providing information and alerts; and
  a processor configured to
    detect a period of rest of the person, based on measurement data from the accelerometer,
    analyse the measured heartbeat interval to determine a probability of having arrhythmia for the person;
    generate an alert to the user interface, if the probability exceeds a predetermined threshold value, to alert the person to measure the electrocardiogram with the second means for measuring an electrocardiogram;
    analyse the measured electrocardiogram to determine if the probable arrhythmia is confirmed; and
    indicate the confirmed arrhythmia to the person via the user interface.

In another aspect, an embodiment of the present disclosure provides a method for determining a probability of arrhythmia for a person, comprising steps of
  detecting a period of rest of the person, using an accelerometer,
  measuring heartbeat interval of the person for a period of time,
  analysing the measured heartbeat interval to determine a probability of having arrhythmia for the person,
  alerting the person to measure an electrocardiogram if the probability exceeds a predetermined threshold value,
  measuring an electrocardiogram of the person,
  analysing the measured electrocardiogram to detect if the probable arrhythmia is confirmed, and
  creating an alert if the arrhythmia is confirmed.

Embodiments of the present disclosure substantially eliminate or at least partially address the aforementioned problems in the prior art, and enable reliable determination of probability of arrhythmia for a person.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
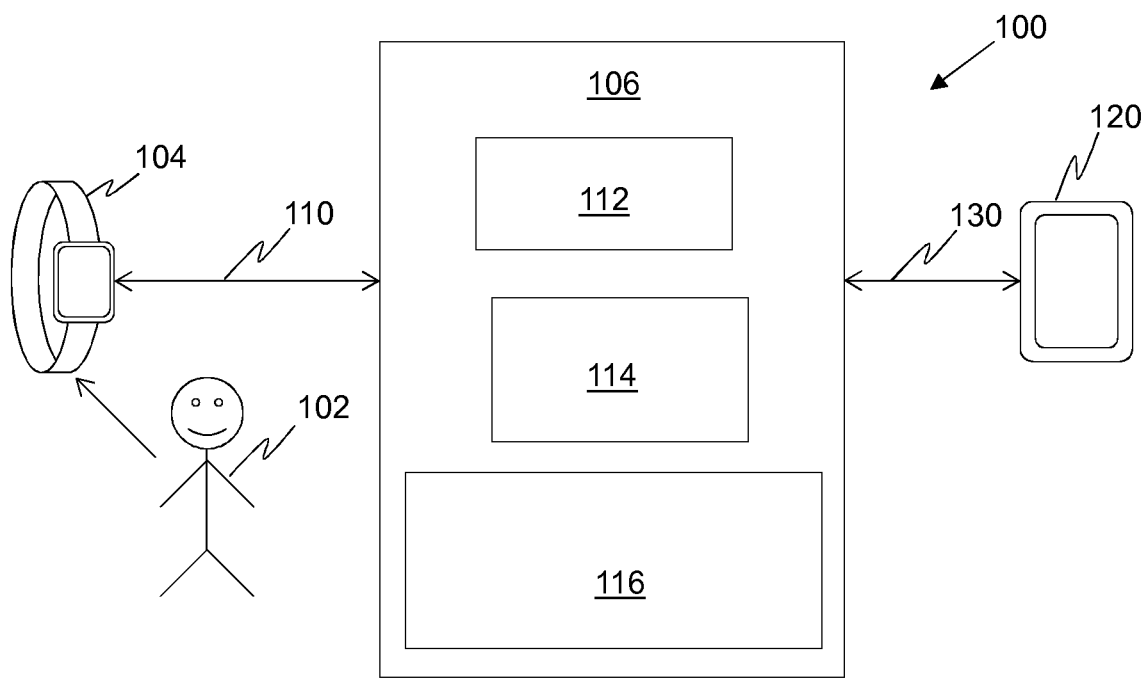
FIG. 1 is schematic illustration of a system for determining a probability of arrhythmia for a person, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a system for determining a probability of arrhythmia for a person, comprising
   a wearable device comprising
      means for measuring heartbeat interval of the person for a period of time;
      an accelerometer;
   means for measuring an electrocardiogram of the person;
   a user interface for providing information and alerts; and
   a processor configured to
      detect a period of rest of the person, based on measurement data from the accelerometer,
      analyse the measured heartbeat interval to determine a probability of having arrhythmia for the person;
      generate an alert to the user interface, if the probability exceeds a predetermined threshold value, to alert the person to measure the electrocardiogram with the second means for measuring an electrocardiogram;
      analyse the measured electrocardiogram to determine if the probable arrhythmia is confirmed; and
      indicate the confirmed arrhythmia to the person via the user interface.

In another aspect, an embodiment of the present disclosure provides a method for determining a probability of arrhythmia for a person, comprising steps of
   detecting a period of rest of the person, using an accelerometer,
   measuring heartbeat interval of the person for a period of time,
   analysing the measured heartbeat interval to determine a probability of having arrhythmia for the person,
   alerting the person to measure an electrocardiogram if the probability exceeds a predetermined threshold value,
   measuring an electrocardiogram of the person,
   analysing the measured electrocardiogram to detect if the probable arrhythmia is confirmed, and
   creating an alert if the arrhythmia is confirmed.

The present disclosure relates to a system and a method for determining a probability of arrhythmia for a person. Specifically, the present disclosure enables in monitoring and alerting a person about confirmed arrhythmia condition. The confirmation of the arrhythmia condition is associated with two phase determination, initial phase being measuring a probability of having arrhythmia based on measured heartbeat and later phase being confirming the arrhythmia based on measured electrocardiogram, computed (or compared) with the measured heartbeat. Therefore, based on the present disclosure, people most likely to have a heart problem, can efficiently monitor their heart condition. Further, people having a heart problem can keep strict vigil on their heart condition. Accordingly, the present disclosure enables people to timely take necessary action and decisions to maintain healthy heart condition.

Furthermore, the system comprises an accelerometer, which measurement data is used to detect or determinate a period of rest of the person. Indeed, this leads to a significant improvement of the results of the method, as the heartbeat interval is determined only when the person is at rest, i.e. there are less interference in the measurement results due to movement of the measurement means and thus the quality of the measured signal is improved. Furthermore, the use of an accelerometer in this way enables energy savings, which in turn makes the system more reliable.

According to an embodiment, the system may function as follows, when the wearable device is worn on a wrist. The accelerometer indicates that movement is minimal, when the resultant acceleration is below a pre-defined acceleration threshold X. The acceleration threshold X is typically set for each device separately, and most typically it is set during manufacturing of the device.

After detecting that the user is not moving or is only moving very slightly (acceleration is below the acceleration threshold X), the means for measuring heartbeat interval is activated. The resulting measurement shows that amplitude of the pulse waves is good, i.e. the peak-to-peak amplitude of the signal is over a pre-defined amplitude threshold Y. The amplitude threshold Y is also typically device specific and set during manufacture of the system.

Thereafter, pulse detection from the measured photoplethysmogram (PPG) signal S takes place, and is analysed for example in the following manner. Firstly, a derivative S' of the signal is obtained. Likewise, the pulse area A is compared to a pulse area threshold Q. If the derivative S' is above a derivative threshold Z and the pulse area A is above the pulse area threshold Q, the pulse is deemed valid for further analysis. Thereafter, a possible irregularity of the pulse is determined by comparing a median beat correlation to the beats, i.e. pulse-to-pulse time series (pulse wave) is detected. A high correlation indicates a regular pulse whereas a low correlation indicates an irregular pulse. The correlation is then compared against an irregularity threshold I, which is also device specific and as explained below, can also be user specific. Finally, a warning signal is sent if the pulse-to-pulse time series or pulse waves are found to be irregular, i.e. above the irregularity threshold I.

In an embodiment, the arrhythmia condition includes irregular heartbeat, such as, too fast or too slow heartbeat. Arrhythmia may include a condition of too fast heartbeats such as tachycardia (over 100 beats per minute in adults), and bradycardia (less than 60 beats per minute in adults). Generally, symptoms of arrhythmia may include palpitations, chest pains, shortness of breath, fluttering in chest and so forth.

The system of the present disclosure includes means for measuring heartbeat interval of the person for a period of time. The term "heartbeat interval" used herein refers to a time interval between two consecutive heartbeats. For example, normal resting heart rate (beats per minute) for adults' ranges from 60 to 100 beats a minute. Therefore, the "heartbeat interval" would be 1 to 0.6 second. The system may be set to measure the heartbeat interval (when not measured continuously) for a limited period of time. This period of time can be for example 30 seconds, one minute, three minutes, five minutes or ten minutes.

In an embodiment, the means for measuring heartbeat interval is a wearable means (or device) capable of being worn at a suitable body part from where person's (or user's) biosignals can be received. It is to be understood that the biosignals may include data from which the heartbeat interval of the person can be derived. In an example, the biosignals may include a rate of blood flow associated with a particular blood vessel. According to an embodiment, the wearable device is selected from a wristband, an ankleband, a ring and a chest belt.

In one embodiment, the means for measuring heartbeat interval is selected from electrical measurement means, optical measurement means, and ballistic measurement means.

In an embodiment, the electrical measurement means for measuring heartbeat interval may include electrical contact points (or electrodes) adapted to be placed on (or allowed to made contact with) appropriated body parts, from which electrical biosignals can be sensed or received. For example, the electrical measurement means may include the chest belt having electrical contact points adapted to be appropriately placed on a chest of a person for receiving (or sensing) electrical signals transmitted by heart muscle (due to heart's activity) through the skin.

In an embodiment, the electrical measurement means may determine the heartbeat intervals beat-by-beat. Specifically, the heartbeat interval may be measured by RR intervals, of the QRS waves corresponding to the heartbeats. For example, the electrical measurement means may include a built-in QRS detector, which detects the sharp R-waves and intervals between successive R-waves (i.e. RR intervals). In an embodiment, R-wave detection is based on slope detection, such as, detecting a maximum positive derivative of a rising R-wave followed by detecting a maximum negative derivative of a falling R-wave. In this context, R is a point corresponding to the peak of the QRS complex of the ECG wave; and RR is the interval between successive Rs and the QRS complex is the series of deflections in an electrocardiogram that represent electrical activity generated by ventricular depolarization prior to contraction of the ventricles, as is customary in the art.

In an embodiment, the optical measurement means for measuring heartbeat interval may include optical electronics adapted to be placed on (or allowed to made contact with) appropriate body parts, from which optical biosignals can be sensed or received. For example, the optical measurement means may include one of the wristband, the ankleband or the ring, allowed to make contact with a particular blood vessel. Further, the optical measurement means may include optical electronics, such as at least one light source and at least one light detector. The at least one light source may be made to contact at least a blood vessel, such a common digital nerve or a palmar metacarpal artery of the user's finger for collecting appropriate measurement data (when the optical measurement means is the ring). In operation, a light pulse can be sent from the at least one light source and thereafter reflected or transmitted light can be received by the at least one light detector to collect appropriate measurement data.

In an embodiment, the optical measurement means measure the heartbeat interval using pulse wave measurement, i.e. measured optically by photoplethysmography (PPG). Specifically, the heartbeat interval (i.e. pulse intervals) are extracted by heartbeats detected from rising edge of the pulse waves (due to increased blood volume in systole phase) or from maximum points of the pulse waves. For example, the heartbeat intervals may be computed as differences between successive pulses (pulse intervals). More specifically, the variations in volume of the blood vessels (during the flow of blood) result in variation in the measured reflectance or transmission (i.e. light intensity) which is measured and processed to generate the PPG. It may be evident that the optical means for measuring heartbeat interval may also include other electronic components such as a microprocessor, a controller, memories and a communication module, as is possible also for the other measurement means in this description. The means for measuring heartbeat interval (i.e. optical measurement means) may for example be a portable computing device equipped with a camera and a processor configured to determine the heartbeat interval.

In an embodiment, the ballistic measurement means measures heartbeat interval using heartbeats measured using ballistocardiography (ballistic measurement). Specifically, the heartbeat intervals are extracted from heartbeats detected from ballistic peaks recurring in the ballistic measurement at heartbeat frequency. For example, before detection, movements due to respiration or body posture changes are filtered out, and heartbeat intervals are computed as time differences between ballistic observations related to successive heartbeats. In other words, the ballistocardiography may employ a technique for producing a graphical representation of repetitive motions of the human body arising from the sudden ejection of blood into the great vessels (such as aorta, pulmonary arteries, pulmonary veins and so forth) with each heartbeat. In the present disclosure, repetitive motions of the human body are associated with repetitive motions arising from the cardiac and respiratory cycles of the user. The ballistic measurement means may also be based on the use of a radar technology. Such measurement means may also be contactless measurement means.

The system also comprises means for measuring an electrocardiogram of the person. In one embodiment, the means for measuring an electrocardiogram may include a pair of electrically conductive elements adapted to sense electrical signals transmitted by heart muscle through user's skin. In an example, the user may contact the pair of electrically conductive elements with two body parts, such as two thumbs or index fingers for the generation of the electrocardiogram. The pair of electrically conductive elements may be operatively coupled to a processing unit capable of processing the sensed electrical signals to generate the electrocardiogram, which is explained in greater detail herein later.

In another embodiment, the means for measuring an electrocardiogram may include a device having 10 electrodes (i.e. a conventional 12-lead ECG) to be placed on the user's limbs and on a surface of the chest. The overall magnitude of the heart's electrical potential may be measured from 12 different angles ("leads") and recorded over a period of time (usually 10 seconds). Accordingly, the overall magnitude and direction of the heart's electrical depolarization may be captured at each moment throughout the cardiac cycle. A graph of voltage versus time produces an electrocardiogram.

The system further comprises a user interface for providing information and alerts. The user interface may be associated with a display of a portable communication device, such as a smart phone, a tablet, a laptop and the like, associated with the user. The user interface, for example the display of such device, may enable in providing the information and alerts. In an example, the information and alerts may be related to the probability of arrhythmia. For example, the information may include information related to user's heart, such as electrocardiogram, heart-rate and so forth. Further, the alerts may include text matter, such as an alert message. Additionally, the alerts may include light and/or sound signals to be generated by the portable communication device.

In an embodiment, where the user interface is associated with the portable communication device (such as the smart phone) of the user, the means for measuring an electrocardiogram (such as the pair of electrically conductive elements) may be mounted on the portable communication device, for example at a back of the portable communication device. Further, the pair of electrically conductive elements may be operatively coupled to the processing unit of the portable communication device for processing the sensed electrical signals to generate the electrocardiogram.

The system further comprises a processor configured to detect a period of rest of the person, based on measurement data from the accelerometer. The accelerometer is thus configured to communicate with the processor. The communication can be continuous or intermittent, and it is possible that the communication intervals be set by the user. Indeed, a person more prone to arrhythmia can select the accelerometer to continuously measure and communicate the measurement data to the processor, and the processor is then configured to carry out the further steps of the method whenever a period of rest of the person is detected (or at all times, although this is not the preferred embodiment). When the communication intervals are set to be intermittent, these can be for example every five minutes, every 30 minutes, every hour, every three hours, every six hours or every twelve hours. The system may also comprise information about the time zone of the person, and take this into account when deciding when the measurement of the heartbeat interval is to be carried out (day/night). Likewise, it may comprise information about the persons' work rhythm (for example that the person is working irregular shifts, which may increase the risk of arrhythmia).

The processor is further configured to analyse the measured heartbeat interval to determine a probability of having arrhythmia for the person. Specifically, the processor may be configured to analyse the heartbeat interval measured by the means (i.e. the wearable device having one of the electrical, optical and ballistic measurement means) for measuring the heartbeat interval. For example, the processor may be configured to initially analyse the heartbeat interval measured with the wearable device, such as the wristband, the ankleband, the ring and the chest belt, to determine the probability of having arrhythmia based on the analysed heartbeat interval.

In one embodiment, the processor may be a server communicably coupled to the portable communication device (such as the smart phone having the user interface) of the user. The processor may be communicably coupled to the portable communication device via a long range wireless communication network, such as Wireless Local Area Network (WLAN) or cellular networks including Global System for Mobile Communications (GSM), General Packet Radio Service (GPRS), Universal Mobile Telecommunications System (UMTS) and so forth. The portable communication device may be communicably coupled the wearable device. Further, the portable communication device may be communicably coupled to the wearable device via a short-range wireless communication network such as Bluetooth, infrared, near field communication, ultraband, ZigBee and so forth. Accordingly, the measured heartbeat interval from the wearable device may be communicated (or transmitted) to the portable communication device of the user, and thereafter the portable communication device may transmit the measured heartbeat interval to the processor (such as the server) for the analysis thereof. According to an embodiment, the probability of having arrhythmia may be determined (or derived) based on various aspects associated with the measured heartbeat interval. Specifically, based on variation in the measured heartbeat interval, a user may be subject to different arrhythmia conditions. For example, a probability of an arrhythmia condition, such as sinus arrest (sinoatrial arrest or sinus pause), may be determined from measured heartbeat interval if RR interval is longer than 3 seconds. The measured heartbeat interval falling into this category may be due to sinus arrest or atrioventricular block (AV-block).

In another embodiment, a probability of an arrhythmia condition, such as bradycardia (or bradyarrhythmia), may be determined from the measured heartbeat interval if heart rate is constantly below a specified threshold, for example 35 beats/minute. In one embodiment, the processor may be configured to include other threshold values, for example 31 to 39 beats/minute, to determine the probable arrhythmia condition to be bradycardia.

In one embodiment, a probability of an arrhythmia condition, such as tachycardia (or tachyarrhythmia), may be determined from the measured heartbeat interval if heart rate is constantly above a specified threshold, for example 100 beats/minute, without being related to physical activity or hemodynamic state. In one embodiment, the processor may be configured to include other threshold values, for example 90 to 99 beats/minute, to determine the probable arrhythmia condition to be tachycardia.

In another embodiment, a probability of an arrhythmia condition, such as extrasystole and ectopic beats, may be determined from the measured heartbeat interval if single irregular sequences of short RR interval are followed by long RR interval, where before and after such a sequence the RR interval is regular. The measured heartbeat interval falling into this category may be due to both premature atrial contractions and ventricular contractions.

In one embodiment, a probability of an arrhythmia condition, such as atrial fibrillation, may be determined from the measured heartbeat interval if the heartbeat is rapid and comprises irregular beating. The detection of atrial fibrillation includes analysis of the beat-to-beat heartbeat time intervals or RR-intervals using one of the techniques of variability and complexity (or irregularity). In the variability technique, one or more analysis parameters are computed from the heartbeat interval time series, which quantify the variability within the time series data points, i.e. how much the RR intervals change within the measurement period. In addition to overall variability measures such as standard deviation of data points, differences between successive heartbeat intervals are also computed to have a measure of beat-by-beat variability. In complexity (or irregularity) technique, the complexity or irregularity of the heartbeat interval time series is quantified using one or more nonlinear analysis methods such as entropy measurement (which measures complexity or how chaotic the time series is) or beat-to-beat scattergrams. Further, the probability of AF is computed as a weighted sum of the two or more analysis parameters described in the variability or complexity techniques. For example, thresholds for the different analysis parameters (values indicating arrhythmia vs. values indicating normal rhythm) as well as the weights (how significant the parameter is compared to others) are derived based on real patient data available in arrhythmia data bases.

As mentioned herein above, the means (i.e. the electrical, optical or ballistic means) measures the heartbeat interval of the person for a period of time. In an embodiment, the period of time may be from 10 seconds to 60 minutes. The period of time can be for example from 10, 20, 30 40, 50, 60 seconds or 2, 3, 4, 5, 6, 7, 8, 9, 10, 15, 20, 25, 30, 35, 40, 45 or 50 minutes up to 20, 30 40, 50, 60 seconds or 2, 3, 4, 5, 6, 7, 8, 9, 10, 15, 20, 25, 30, 35, 40, 45, 50, 55 or 60 minutes. In another embodiment, the means may measure the heartbeat interval continuously. It may be evident that the period of time may be sufficient to yield a measure of heartbeat interval from which the probability of having arrhythmia may be determined.

The processor is further configured to generate an alert to the user interface, if the probability exceeds a predetermined threshold value, to alert the person to measure the electrocardiogram with the means for measuring an electrocardiogram. As mentioned herein above, the probability of the arrhythmia conditions (such as sinus arrest, tachycardia, bradycardia, extrasystole and atrial fibrillation) may be based on the measured heartbeat interval, therefore the predetermined threshold value may be associated with the measured heartbeat interval. For example, the processer may be configured to include a predetermined threshold value of 3 (or more, such as 4) seconds (for time between RR intervals) for the measured heartbeat interval to determine the probability of the arrhythmia condition to be sinus arrest (or sinus pause). Further, the processer may be configured to include a predetermined threshold value of 30-39 beats/minute, to determine the probable arrhythmia condition to be bradycardia. Similarly, the processer may be configured to include other predetermined threshold values corresponding to other arrhythmia conditions, such as the tachycardia, the extrasystole and the atrial fibrillation.

In an embodiment, as mentioned herein above, the alert (to measure the electrocardiogram with the means for measuring an electrocardiogram) may be presented on the user interface (such as display of the portable communication device of the user) as alert text massage. Alternatively, the alerts may include light and/or sound signals to be generated by the portable communication device.

The user therefore measures the electrocardiogram (with the means for measuring an electrocardiogram) based on the generated alert. For example, the user may contact the pair of electrically conductive elements mounted at the back of the portable communication device with his or her two body parts (for example fingers) to generate the electrocardiogram. Specifically, the electrical signals sensed by the pair of electrically conductive elements may be processed by the processing unit of the portable communication device to generate the electrocardiogram. In another embodiment, the user may visit a clinic, hospital or test centre, to get the electrocardiogram measured with the conventional device (i.e. 12-lead ECG), based on the alert. According to an embodiment, the means for measuring an electrocardiogram (for example the conventional 12-lead ECG device) may comprise a communication interface. For example, the communication interface may be combination of a wired (such as Local Area Network or LAN) or wireless communication means (such as wireless Local Area Network or WLAN).

The communication interface of the means for measuring an electrocardiogram may be communicably coupled to the processor and may be further configured to send a measured electrocardiogram to the server, to be analysed to determine if the probable arrhythmia is confirmed.

The processor is further configured to analyse the measured electrocardiogram to determine if the probable arrhythmia is confirmed. Specifically, the probable arrhythmia determined by the analysis of the measured heartbeat interval (such as the photoplethysmogram) is confirmed, if the electrocardiogram is in sync with the measured heartbeat interval (i.e. the photoplethysmogram). Otherwise, there may be a defect in the analysis of the measured heartbeat interval.

In an embodiment, the measured electrocardiogram is analysed by the processor to determine a signal-to-noise ratio of the electrocardiogram measurement. Specifically, the measured electrocardiogram may be analysed to determine at least one of noise, interference and movement artefacts during the electrocardiogram. In an example, such noise may be caused by detachment of one or more electrodes from the user's body, improper placement of the electrodes on the user's body, movement (such as shivering) by the user, skin impedance that may be caused by greasy skin, incorrect calibration of the means for measuring the electrocardiogram, noise originating from environment and so forth. In one embodiment, the processor may be configured to filter out such noise.

In one embodiment, the measured electrocardiogram is analysed by the processor to determine heartbeat intervals (or RR interval) of a person for a period of time. Further, the heartbeat intervals are used to determine a probability of having arrhythmia for the person.

According to an embodiment, the measured electrocardiogram is analysed by the processor to determine a QRS complex morphology for the heartbeats for an identification of arrhythmia. Further, QRS duration may also be analysed for the identification of arrhythmia. In an example, if the QRS duration is less than 120 milliseconds and the QRS complex morphology is similar to that of normal heartbeats, the arrhythmia may be identified as premature atrial contractions (PACs). In another example, if the QRS duration is more than 120 milliseconds and the QRS complex morphology differs substantially from that of normal heartbeats, the arrhythmia may be identified as premature ventricular contractions (PVCs). In yet another example, if the QRS complex morphology does not differ among heartbeats, the arrhythmia may be identified as atrial fibrillation.

Additionally, the processor is configured to indicate the confirmed arrhythmia to the person via the user interface. Specifically, the processor may be configured to send a message to a portable communication device associated with the person, to be displayed on the user interface thereof. In an example, the message may include text matter indicating the confirmed arrhythmia to the person. In another example, the message may include sound signals to be generated by the portable communication device associated, such as a voice message indicating the confirmed arrhythmia. In yet another example, the message may include instructions to the person indicating that further diagnosis and/or an urgent treatment may be required.

In an embodiment, the alert is sent to at least one of the person concerned and a third party, wherein the third party is a medical professional or an emergency response centre. Specifically, the alert may be sent to a portable communication device associated with the third party (such as a medical professional or an emergency response centre). In an example, the alert may include information about a serious condition associated with the health of the person, such as a stroke. It may be evident that in such instance, the medical professional or the emergency response centre may be informed about urgent attention required by the person. Further, the medical professional may suggest possible treatments to the person.

In one embodiment, the at least one of the means for measuring an electrocardiogram, the processor and the user interface is arranged in a portable computing device. In other words, the means for measuring an electrocardiogram (such as the pair of electrically conductive elements), the processor (such as the processing unit), and the user interface (such as the display) may be components associated with the portable computing device, such as the portable communication device, for example the smart phone of the user. In such instances, the system of the present disclosure primarily comprises the wearable means for measuring heartbeat interval (i.e. such as one of the wristband, the ankleband, the ring, and the chest belt) and the portable computing device (such as the smart phone of the user having the means for measuring an electrocardiogram, the processor and the user interface). In another embodiment, the means for measuring an electrocardiogram, the processor and the user interface may not be part of the portable computing device. As mentioned herein above, the means for measuring an electrocardiogram, the processor and the user interface may be the conventional device (i.e. 12-lead ECG), the server and the smart phone of the user, respectively.

According to yet another embodiment, the system is configured to update its pre-determined threshold value based on the previous measurements. Indeed, the system may be configured to carry out, for example once a day, a baseline measurement. When a certain number of such baseline measurements are combined and analysed, the natural variations of the user can be determined and thereby a personal threshold value for the alert set for the particular user.

The system may also comprise the possibility for the user to manually start measurement of the heartbeat interval (based on symptoms for example). This may be incorporated for example in the user interface, as an icon or similar.

The system may further comprise a memory configured to store the measurement data (accelerometer, heartbeat interval and/or electrocardiogram).

DETAILED DESCRIPTION OF THE DRAWINGS

Referring to FIG. 1, illustrated is a schematic illustration of a system 100 for determining a probability of arrhythmia for a person 102, in accordance with an embodiment of the present disclosure. The system 100 comprises a means 104 (such as a wristband) for measuring heartbeat interval of the person 102, and a portable computing device 106 (such as a portable communication device, for example a smart phone) communicably coupled to the means 104 for measuring heartbeat interval. The means 104 for measuring heartbeat interval is communicably coupled to the portable computing device 106 via a short-range wireless communication network 110 (for example such as Bluetooth or Zigbee). As shown, the portable computing device 106 includes a processor 112, a user interface 114, and a means 116 (such as the pair of electrically conductive elements) for measuring an electrocardiogram of the person 102. The system 100 also comprises a mobile communication device 120 (such as a smart phone) associated with a third party (such as a medical professional or an emergency response centre). The mobile communication device 120 is communicably coupled to the portable computing device 106 via a long-range wireless communication network 130 (such as cellular networks including Global System for Mobile Communications).

Figure 2:
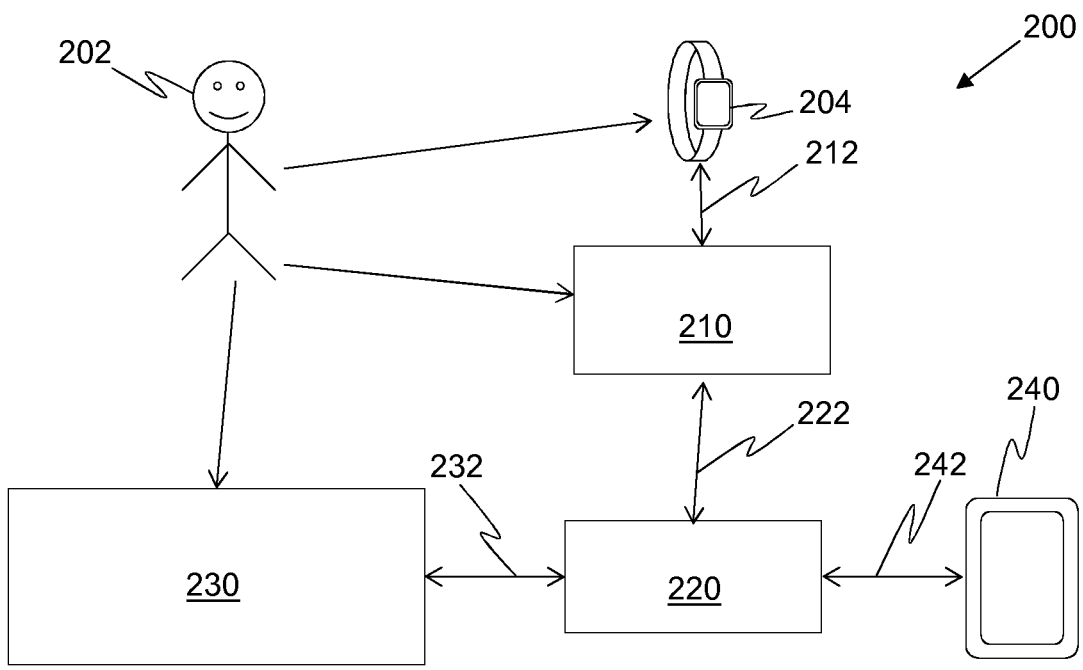
FIG. 2 is schematic illustration of a system for determining a probability of arrhythmia for a person, in accordance with another embodiment of the present disclosure.

FIG. 2 is schematic illustration of a system 200 for determining a probability of arrhythmia for a person 202, in accordance with another embodiment of the present disclosure. As shown, the system 200 includes a means 204 (such as a wristband) for measuring heartbeat interval of the person 202. The system 200 also includes a user interface 210, such as a display of a portable communication device, for example, a smart phone associated with the user 202. The means 204 for measuring heartbeat interval is communicably coupled to the user interface 210 via a short-range wireless communication network 212. The system 200 further includes a processor 220 (such as a server) communicably coupled to the user interface 210 via a long-range wireless communication network 222. The system 200 also includes a means for measuring electrocardiogram 230 (such as 12-lead ECG device) communicably coupled to the processor 220 via a communication interface 232. The system 200 also comprises a mobile communication device 240 (such as a smart phone) associated with a third party, and communicably coupled to the processor via a long-range wireless communication network 242.

Figure 3:
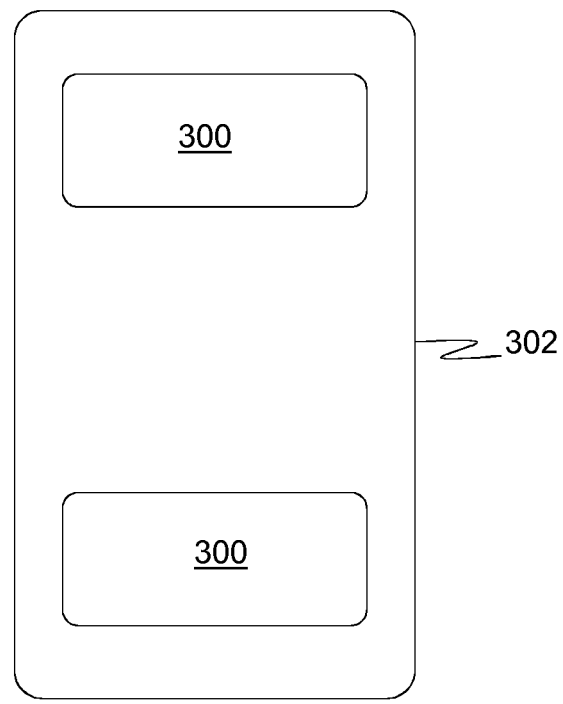
FIG. 3 is a schematic illustration of an accessory for measuring an electrocardiogram, in accordance with an embodiment of the present disclosure.

FIG. 3 is a schematic illustration of an accessory 300 for measuring an electrocardiogram, in accordance with an embodiment of the present disclosure. The accessory 300 includes a pair of electrically conductive elements mounted at a back of a portable computing device 302 (such as the portable computing device 106, shown in FIG. 1, for example a smart phone). The accessory 300 may receive two figures, such as two thumbs or two index fingers, thereon for sensing electrical signals corresponding to heart activities for the generation of electrocardiogram.

Figure 4A:
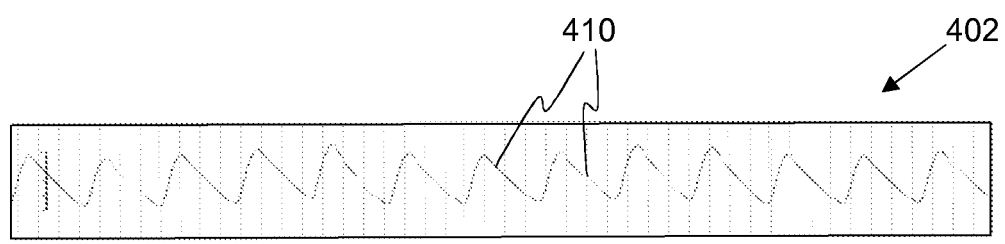
FIGS. 4A-B are schematic illustrations of a photoplethysmogram and an electrocardiogram, respectively, which does not depict probability of arrhythmia, in accordance with an embodiment of the present disclosure.
Figure 4B:
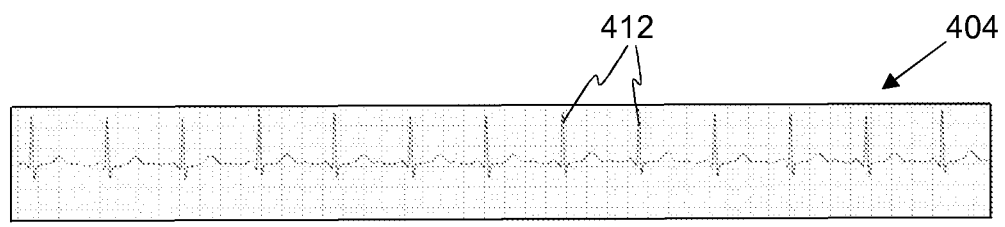

FIGS. 4A-B are schematic illustrations of a photoplethysmogram 402 and an electrocardiogram 404, respectively, which does not depict probability of arrhythmia, in accordance with an embodiment of the present disclosure. The photoplethysmogram 402 is derived (or generated) from heartbeat interval measured using a means for measuring heartbeat interval (such as the means 104, shown in FIG. 1). The electrocardiogram 404 is measured (or generated) via a means for measuring an electrocardiogram (such as the means 116 or 230, shown in FIGS. 1 and 2). As shown, both photoplethysmogram 402 and the electrocardiogram 404 include heartbeats 410, 412, respectively, that are spaced at equal intervals, thereby indicating a normal heart condition (or lack of probability of arrhythmia).

Figure 5A:
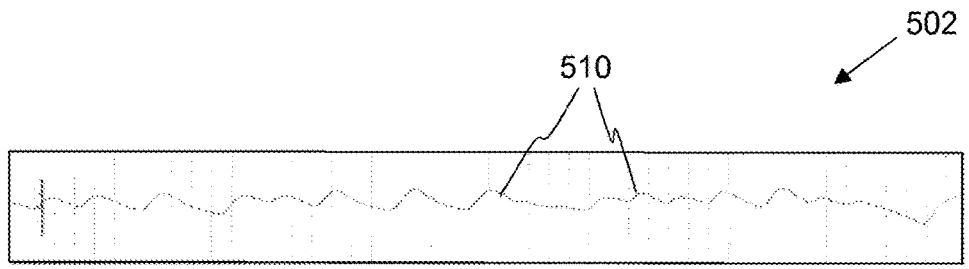
FIGS. 5A-B are schematic illustrations of a photoplethysmogram and an electrocardiogram, respectively, which depict probability of arrhythmia, in accordance with an embodiment of the present disclosure.
Figure 5B:
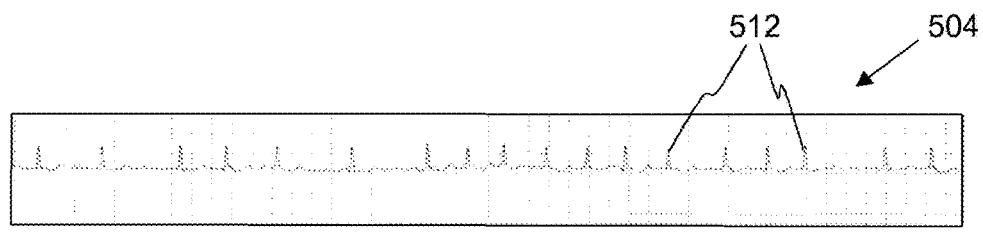

FIGS. 5A-B are schematic illustrations of a photoplethysmogram 502 and an electrocardiogram 504, respectively, which depict probability of arrhythmia, in accordance with an embodiment of the present disclosure. The photoplethysmogram 502 is derived from heartbeat interval measured using a means for measuring heartbeat interval (such as the means 104, shown in FIG. 1). The electrocardiogram 504 is measured via a means for measuring an electrocardiogram (such as the means 116 or 230, shown in FIGS. 1 and 2). The electrocardiogram 504 is measured when a probability of having arrhythmia (based on the heartbeat interval) exceeds a predetermined threshold value. For example, when the analysis of the measured heartbeat interval (used for generating the photoplethysmogram 502) indicates the probability of having arrhythmia. As shown, both photoplethysmogram 502 and the electrocardiogram 504 include abnormal heartbeats 510, 512, respectively, i.e. spaced at unequal intervals, thereby indicating an abnormal heart condition (or confirmed arrhythmia condition).

Figure 6:
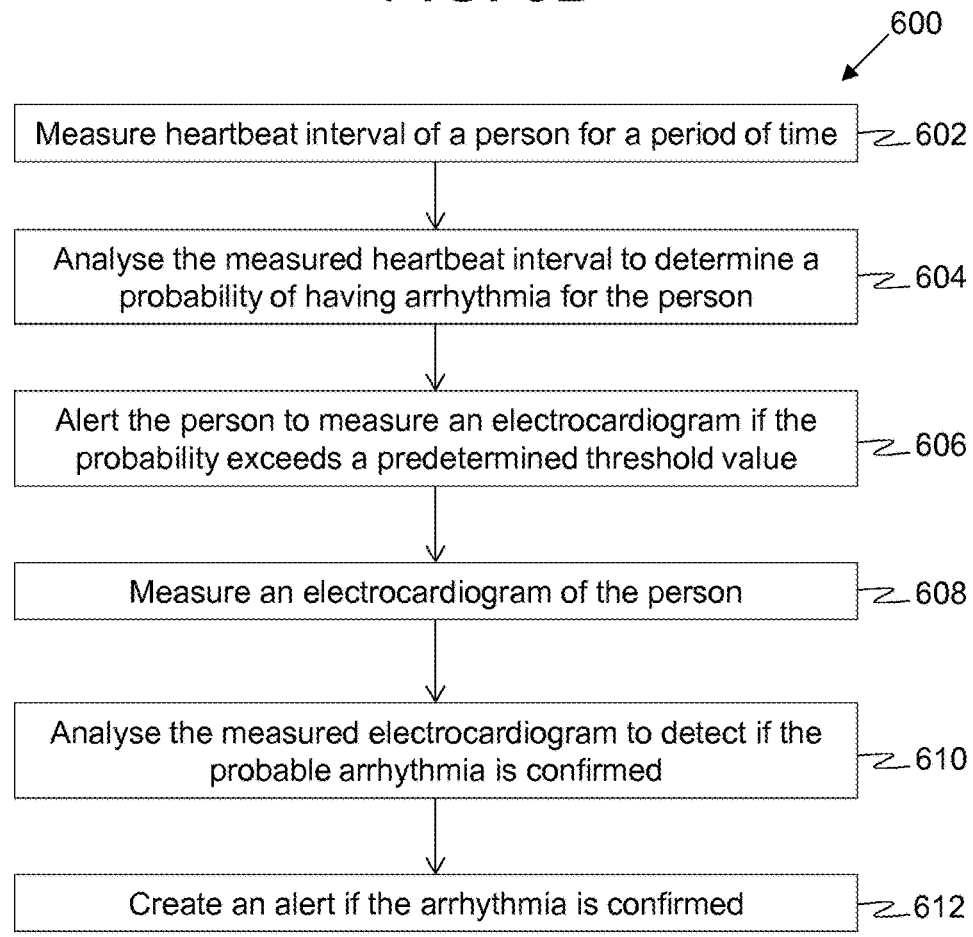
FIG. 6 is an illustration of steps of a method for determining a probability of arrhythmia for a person, in accordance with an embodiment of the present disclosure.

Referring to FIG. 6, illustrated is an illustration of steps of a method 600 for determining a probability of arrhythmia for a person, in accordance with an embodiment of the present disclosure. Those skilled in the art would recognize that the method 600 illustrates steps involved in implementing a system (such as one the systems 100 or 200) explained herein above in conjunction with the FIGS. 1-5.

In step 602, heartbeat interval of a person is measured for a period of time. In step 604, the measured heartbeat interval is analysed to determine a probability of having arrhythmia for the person. In step 606, if the probability exceeds a predetermined threshold value, the person is alerted to measure an electrocardiogram. In step 608, an electrocardiogram of the person is measured. In step 610, the measured electrocardiogram is analysed to detect if the probable arrhythmia is confirmed. In step 612, an alert is created if the arrhythmia is confirmed.

The steps 602 to 612 are only illustrative and other alternatives can also be provided where one or more steps are added, one or more steps are removed, or one or more steps are provided in a different sequence without departing from the scope of the claims herein. In an embodiment, the method 600 may further comprise sending the alert to at least one of the person and a third party, wherein the third party may be a medical professional or an emergency response centre. Further, the method 600 may comprise a measuring the heartbeat interval continuously.

Figure 7:
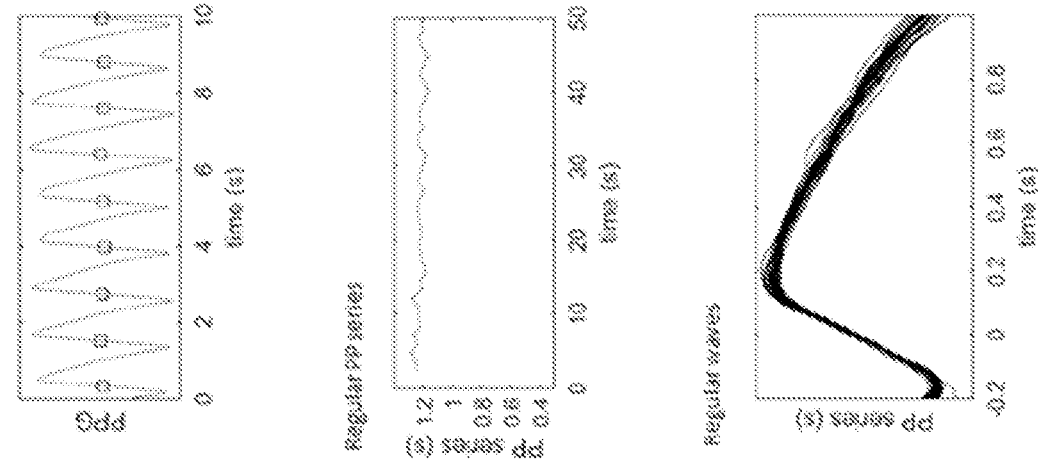
FIG. 7 is an illustration of use of the system according to an embodiment of the present disclosure.
Figure 7:
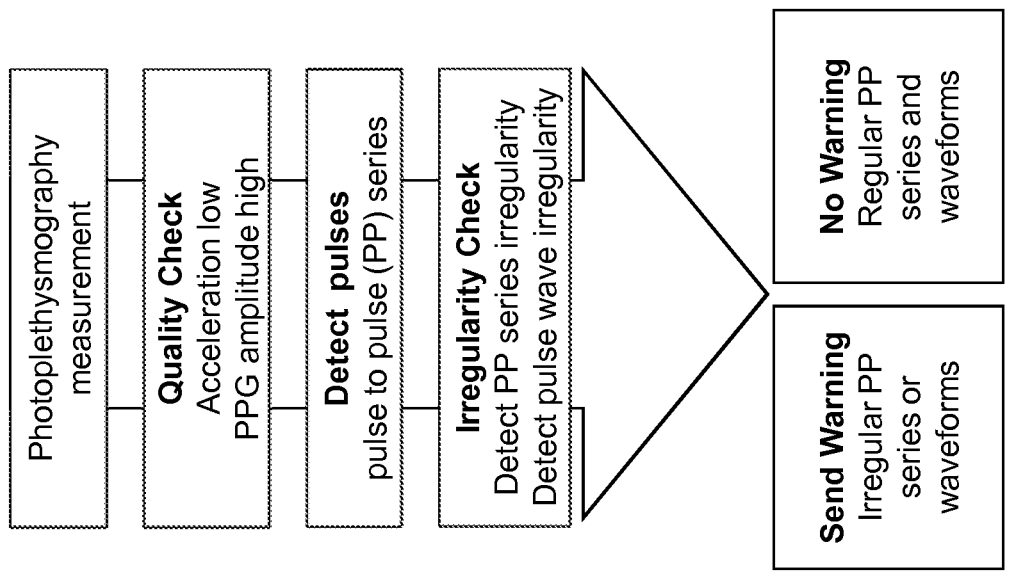
Figure 7:
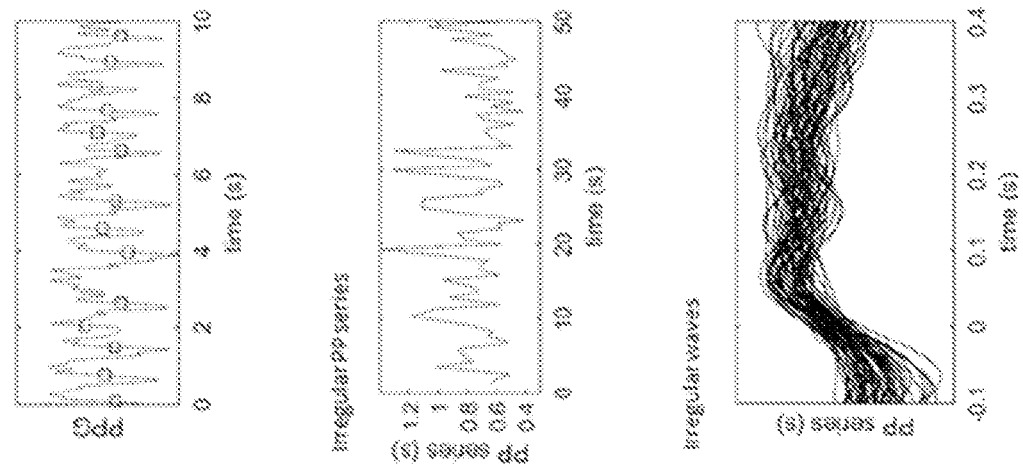

FIG. 7 is an illustration of use of the system according to an embodiment of the present disclosure. The Figure illustrates the embodiment where a photoplethysmogram (PPG) is obtained from the wearable device, in this embodiment for a period of 10 seconds. On the left is shown a situation where the probability of arrhythmia is increased while on the right, is shown a situation where there is no or very low probability of arrhythmia. The system firstly checks the quality of the measurement by confirming that the acceleration is low (i.e. the person is at rest) and the PPG amplitude is high. Thereafter, the system detects the pulse of the user for a period of time (here for 50 seconds) and measures the pulse-to-pulse (PP) series. If the PP series shows irregularities and the pulse wave shows irregularities, the system generates an alert and in this embodiment, also alerts the user that either there are irregular PP series or irregular waveforms or both. If no irregularities are detected, there is no warning generated.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A system for determining a probability of arrhythmia for a person, the system comprising:
   a wearable device comprising:
      means for measuring a heartbeat interval of the person; and
      an accelerometer;
   means for measuring an electrocardiogram of the person;
   a user interface for providing information and alerts; and
   a processor configured to:
      detect a period of rest of the person, based on the accelerometer continuously measuring and communicating measurement data to the processor; and, only when a period of rest of the person is detected:
      measure, only during the period of rest, a resting heartbeat interval of the person for a period of time;
      analyze the measured resting heartbeat interval to determine a probability of having arrhythmia for the person;
      generate an alert, during the period of rest, to the user interface based on the analyzed measured resting heartbeat interval, if the probability exceeds a predetermined threshold value, to alert the person to measure the electrocardiogram with the means for measuring an electrocardiogram;
      analyze the measured electrocardiogram to determine if the probable arrhythmia is confirmed;
      determine whether the electrocardiogram is in sync with the measured resting heartbeat interval; and
      indicate the confirmed arrhythmia to the person via the user interface.

2. The system according to claim 1, wherein the means for measuring heartbeat interval is selected from electrical measurement means, optical measurement means and ballistic measurement means.

3. The system according to claim 1, wherein the wearable device is selected from a wristband, an ankleband, a ring and a chest belt.

4. The system according to claim 1, wherein the means for measuring heartbeat interval is a portable computing device equipped with a camera and a processor configured to determine the heartbeat interval.

5. The system according to claim 1, wherein at least one of the means for measuring an electrocardiogram, the processor and the user interface is arranged in a portable computing device.

6. The system according to claim 1, wherein the processor is further configured to alert a medical professional of a confirmed arrhythmia.

7. The system according to claim 1, wherein the period of time is from 10 seconds to 60 minutes.

8. A method using a system for determining a probability of arrhythmia for a person, comprising:
a wearable device comprising:
means for measuring a heartbeat interval of the person; and
an accelerometer;
means for measuring an electrocardiogram of the person;
a user interface for providing information and alerts; and
a processor configured to;
detect a period of rest of the person, based on the accelerometer continuously measuring and communicating measurement data to the processor; and, only when a period of rest of the person is detected:
measure, only during the period of rest, a resting heartbeat interval of the person for a period of time;
analyze the measured resting heartbeat interval to determine a probability of having arrhythmia for the person;
generate an alert, during the period of rest, to the user interface based on the analyzed measured resting heartbeat interval, if the probability exceeds a predetermined threshold value, to alert the person to measure the electrocardiogram with the means for measuring an electrocardiogram;
analyze the measured electrocardiogram to determine if the probable arrhythmia is confirmed;
determine whether the measured electrocardiogram is in sync with the measured resting heartbeat interval; and
indicate the confirmed arrhythmia to the person via the user interface, for determining if there is a need for measuring an electrocardiogram of the person,
analyzing the measured electrocardiogram to detect if probable arrhythmia is confirmed, and
creating an alert if the arrhythmia is confirmed, by giving an alert to measure an electrocardiogram if there is a probability of arrhythmia for a person, the method comprising steps of:
measuring heartbeat interval of the person for a period of time with the wearable device;
analyzing the measured heartbeat interval, with the processor of the wearable device, to determine a probability of having arrhythmia for the person; and
alerting the person to measure an electrocardiogram, with the user interface of the wearable device, if the probability exceeds a predetermined threshold value.

9. The method according to claim 8, further comprising sending the alert to at least one of the person and a third party.

10. A method according to claim 9, wherein the third party is a medical professional or an emergency response center.

* * * * *